(12) United States Patent
Miles et al.

(10) Patent No.: US 11,931,050 B2
(45) Date of Patent: Mar. 19, 2024

(54) SURGICAL INSTRUMENT FOR ALIGNMENT OF BONE CUTS IN TOTAL JOINT REPLACEMENTS

(71) Applicant: 360 Knee Systems Pty Ltd, New South Wales (AU)

(72) Inventors: Brad Miles, New South Wales (AU); Jialong Li, New South Wales (AU); Willy Theodore, New South Wales (AU)

(73) Assignee: 360 Knee Systems Pty Ltd, New South Wales (AU)

( * ) Notice: Subject to any disclaimer, the term of this patent is extended or adjusted under 35 U.S.C. 154(b) by 513 days.

(21) Appl. No.: 17/253,853

(22) PCT Filed: Jun. 24, 2019

(86) PCT No.: PCT/AU2019/050650
§ 371 (c)(1),
(2) Date: Dec. 18, 2020

(87) PCT Pub. No.: WO2020/000030
PCT Pub. Date: Jan. 2, 2020

(65) Prior Publication Data
US 2021/0267607 A1    Sep. 2, 2021

(30) Foreign Application Priority Data
Jun. 25, 2018   (AU) ................. 2018902271

(51) Int. Cl.
*A61F 2/38*       (2006.01)
*A61B 17/02*      (2006.01)
(Continued)

(52) U.S. Cl.
CPC .......... *A61B 17/155* (2013.01); *A61B 17/025* (2013.01); *A61B 17/157* (2013.01);
(Continued)

(58) Field of Classification Search
CPC ................ A61F 2/3859; A61F 2/4684; A61F 2002/3863
See application file for complete search history.

(56) References Cited

U.S. PATENT DOCUMENTS

2005/0113846 A1    5/2005   Carson
2010/0305575 A1   12/2010   Wilkinson et al.
(Continued)

FOREIGN PATENT DOCUMENTS

WO    2013/044174 A2    5/2005
WO    2017/004669 A1    1/2017

OTHER PUBLICATIONS

International Search Report issued in PCT/AU2019/050650 dated Aug. 15, 2019, 18 pages.
(Continued)

*Primary Examiner* — Samuel S Hanna
(74) *Attorney, Agent, or Firm* — Nixon Peabody LLP (57) ABSTRACT

This disclosure relates to surgical instruments for alignment of bone cuts during surgeries on joints and in particular, during total replacement of joints. The surgical instrument comprises a contact surface shaped to fit a prepared end of the first bone of the joint and an artificial articular surface that imitates the native articular surface of the first bone that has been removed by the preparation of the first bone. The artificial articular surface is pivotable in relation to the surgical instrument. The instrument can be fitted onto the prepared bone and coronal balancing can be performed. After fixing a further instrument to the second bone the joint can be balanced in flexion. At the optimal flexion angle, the slope and the cutting depth can be adjusted to achieve alignment. The further instrument is then used as a guide for cutting the second bone at the resulting cutting depth, slope and *varus/valgus* angle.

16 Claims, 9 Drawing Sheets

(51) Int. Cl.
  *A61B 17/15* (2006.01)
  *A61B 90/00* (2016.01)
(52) U.S. Cl.
  CPC .......... *A61B 90/06* (2016.02); *A61F 2/3859* (2013.01); *A61B 2017/0268* (2013.01); *A61B 2090/062* (2016.02); *A61B 2090/065* (2016.02); *A61B 2090/067* (2016.02); *A61F 2002/3863* (2013.01)

(56) References Cited

U.S. PATENT DOCUMENTS

2011/0066248 A1    3/2011  Ries et al.
2013/0013076 A1*  1/2013  Fisher ................... A61F 2/4657
                                                            623/20.16
2015/0142000 A1    5/2015  Seedhom et al.
2018/0103961 A1*  4/2018  Oh ....................... A61B 17/155

OTHER PUBLICATIONS

Written Opinion issued in PCT/AU2019/050650 dated Aug. 15, 2019, 7 pages.

\* cited by examiner

SURGICAL INSTRUMENT FOR ALIGNMENT OF BONE CUTS IN TOTAL JOINT REPLACEMENTS

RELATED APPLICATIONS

This application is a U.S. National Stage of International Application No. PCT/AU2019/050650, filed Jun. 24, 2019, which claims priority from Australian Provisional Application 2018902271 filed on 25 Jun. 2018, the contents of which are hereby incorporated by reference in their entireties for all purposes.

TECHNICAL FIELD

This disclosure relates to surgical instruments for alignment of bone cuts during surgeries on joints and in particular, during total replacement of joints.

BACKGROUND

Joints between bones often deteriorate over time and need to be replaced. For example, a total knee replacement is a common surgical procedure where articulating surfaces of the knee joint affected by osteoarthritis are replaced by affixed implants. While a reasonable outcome can be achieved in many cases, the knee joint is complex and the total knee replacement has many parameters that can be changed by the surgeon. In particular, the surgeon aims for a 'balanced' knee that is not too tight and not too loose by changing implant positioning intraoperatively. However, it is difficult for the surgeon to find the best combination of multiple parameters including varus/valgus, slope and cut depth as they are interdependent. As a result, multiple cuts to the bones often become necessary leading to either excessive amount of bone being removed, extended duration of the procedure or sub-optimal outcome in terms of knee geometries. Similar difficulties present themselves when replacing other joints, such as shoulder and elbow joints.

In one workflow, the surgeon first cuts the tibia and then determines the position of the femoral component. However, this is often difficult and the above problems arise in many cases. Therefore, there is a need for a medical device that assists the surgeon in achieving a balanced knee without the need for multiple cuts of the same bone.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A surgical instrument for surgery on a joint between a first bone and a second bone comprises:
a contact surface shaped to fit a prepared end of the first bone of the joint.
an artificial articular surface that imitates the native articular surface of the first bone that has been removed by the preparation of the first bone, wherein the artificial articular surface is pivotable in relation to the surgical instrument.

A native articular surface of the second bone of the joint may be concave and the artificial articular surface may be convex to interface with the concave native articular surface of the second bone.

The artificial articular surface may be adjustable and locked in its distraction that defines a distance of the artificial articular surface to the surgical instrument.

A flexion angle of the joint may define a slope of a cut to the second bone.

The slope of the cut may be defined by way of a cutting block that is fixed on the second bone and adjustable in slope.

The cutting block may be adjusted in slope so that the cut is in parallel to a standard plane of the surgical instrument.

The cutting block may be adjustable in cutting depth.

The contact surface may corresponds in shape to the contact surface of a component of an implant.

The artificial articular surface may be similar in shape and location to the native surface of the first bone.

The artificial articular surface may be pivotable such that pivoting of the artificial articular surface increases a distance of the articular surface from the contact surface.

The artificial articular surface may be pivotable about a frontal pivot axis that is located within the artificial articular surface.

The surgical instrument may further comprise a cutting block that is attachable to the second bone of the joint in a first configuration where the cutting block is fixed in relation to a first axis and pivotable about a second axis to adjust a slope of a cut on the second bone based on the pivoting of the artificial articular surface.

The artificial articular surface may comprise pressure sensors to assist in balancing the joint.

The joint may be flexible between a flexed position and an extended position and the articular surface may comprise a first surface component to interface with the second bone in the flexed position and a second surface component to interface with the second bone in the extended position.

The first surface component and the second surface component may be distractable and distraction of one of the first and second surface components causes distraction of the other of the first and second surface components.

The artificial articular surface may be moveable to allow translation to define an interior-exterior rotation of the second bone.

The joint may be a knee, the first bone may be the femur of the knee, and the artificial articular surface may comprise artificial posterior condyles that imitate the posterior surface of the native condyles of the femur.

The surgical instrument may further comprise artificial distal condyles that imitate the distal surface of the native condyles.

For one of medial and lateral sides the artificial posterior condyle and the artificial distal condyles may be distractable and distraction of one of the artificial posterior condyle and the artificial distal condyle may cause distraction of the other of the artificial posterior condyle and the artificial distal condyle.

A method for total replacement of a joint between a first bone and a second bone, the method comprises:
preparing an end of the first bone that forms the joint to create a bone surface that interfaces with a corresponding surface of a surgical instrument, the surgical instrument comprising artificial articular surfaces that are distractible and pivotable; fitting the surgical instrument onto the prepared first bone;

performing coronal balancing by changing the *valgus/varus* angle by adjusting the distraction of the artificial articular surface;

fixing a further instrument to the second bone that has a fixed *valgus/varus* angle according to the adjusted distractions of the artificial articular surface but adjustable cutting depth and adjustable slope;

balancing the joint in flexion by finding an optimal flexion angle under roll-back of the joint defined by the pivotable artificial articular surface acting on the native surface of the second bone;

at the optimal flexion angle, adjusting the slope and the cutting depth of the further instrument such that the further instrument aligns with the surgical instrument fitted to the first bone;

using the further instrument as a guide for cutting the second bone at the resulting cutting depth, slope and *varus/valgus* angle.

There is provided a surgical instrument that has a contact surface shaped to fit a prepared distal end of the femur. In most cases the contact surface would be identical to the contact surface of the femoral component of a chosen implant for the particular patient. The surgical instrument comprises artificial posterior condyles that imitate the native posterior condyles of the femur that have been removed by the preparation of the femur. That is, the artificial posterior condyles are similar in shape and location to the native posterior condyles. However, in contrast to the native posterior condyles, the artificial posterior condyles are pivotable and are locked in their distraction that defines a distance of the artificial posterior condyles to the surgical instrument. As a result of the condyles being pivotable, when the surgical instrument is fitted to the femur, the surgeon can manipulate the knee joint before cutting the tibia by flexing the knee to initiate roll-back of the knee without changing the stiffness of the knee that would be caused by native, non-pivotable posterior condyles acting on the native tibia. This way, the surgeon assesses the tibiofemoral balance between the prepared femur and the native tibia. Due to the pivotable artificial posterior condyles, the amount of posterior condylar angular change relative to the prepared femur as well as the anteroposterior tightness as interpreted by the surgeon defines the slope of the tibial cut. A cutting block can be fixed on the tibia by locating the cutting block relative to the surgical instrument that is fitted to the femur. In the common case where the tibial component is designed with a standard plane, the cutting block is simply located so that the cut is in parallel to the standard plane of the femoral component and the flexion angle then defines the slope of the tibial cut. Further, the cutting depth is adjusted on the cutting block to compensate for parallax offset due to the cutting block being located away from the pivot point of the slope definition.

There is also provided a method for total knee replacement. The method comprises preparing the distal end of the femur to create a bone surface that interfaces with a corresponding surface of a surgical instrument. The surgical instrument comprises distal condyles that are distractable and posterior condyles that are distractable and pivotable. The method then comprises fitting the surgical instrument onto the prepared femur and performing coronal balancing by changing the *valgus/varus* angle by adjusting the distraction of the anterior and/or posterior condyles until the knee is balanced. The method further comprises fixing a tibial instrument to the tibia that has a fixed *valgus/varus* angle according to the adjusted distractions of the artificial condyles but adjustable cutting depth and adjustable slope. The method also comprises balancing the knee in flexion by finding an optimal flexion angle under roll-back of the knee defined by the pivotable artificial posterior condyles acting on the native tibia. Then, the method comprises maintaining the optimal flexion angle while adjusting the slope and the cutting depth of the tibial instrument such that the tibial instrument aligns with the surgical instrument fitted to the femur at the optimal flexion angle. Finally, the tibial instrument is used as a guide for a bone preparation instrument to cut the tibia at the resulting cutting depth, slope and *varus/valgus* angle.

BRIEF DESCRIPTION OF DRAWINGS

An example will now be described with reference to the following drawings.

DESCRIPTION OF EMBODIMENTS

The following description provides a surgical instrument and method for joint replacement. While the details are described with reference to a knee joint, they are equally applicable to other joints. In particular, the described solution may be applied to other hinge joints where is a bone joint in which the articular surfaces are moulded to each other in such a manner as to permit motion only in one plane. More particularly, the described solution may be applied to saddle joints comprising opposing surfaces that are reciprocally concave-convex, such as the carpometacarpal joint of the thumb and other condyloid joints, where an ovoid articular surface, or condyle that is received into an elliptical cavity. This permits movement in two planes, allowing flexion, extension, adduction, abduction, and circumduction. Examples include the wrist-joint, metacarpophalangeal joints and metatarsophalangeal joints. The below disclosure relating to knee replacement can be applied to these joints by simply substituting the "distal end of the femur" below with the convex end of the joint to be replaced and substituting the "tibia surface" with the concave surface of the joint.

Figure 1:
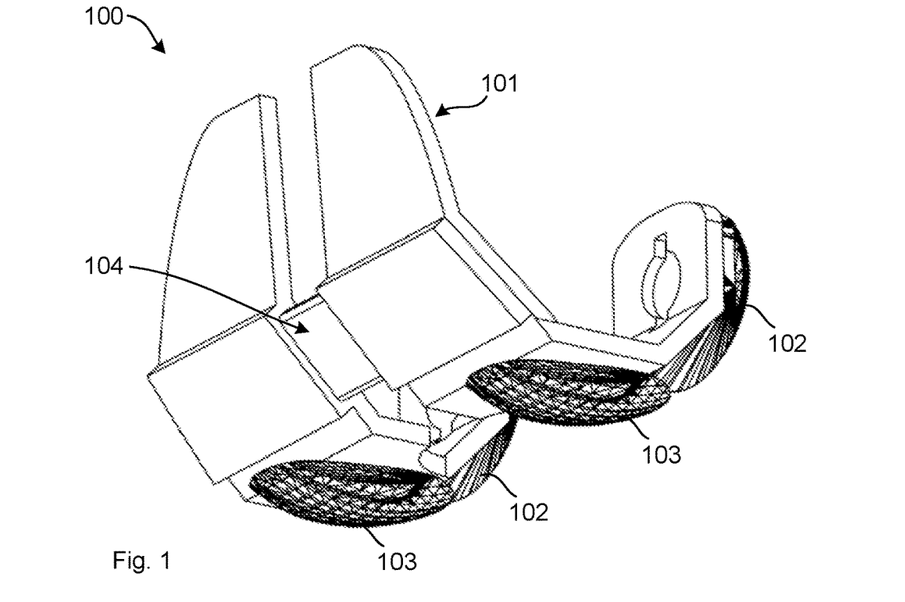
FIG. 1 is a perspective view of a surgical instrument.
Figure 2:
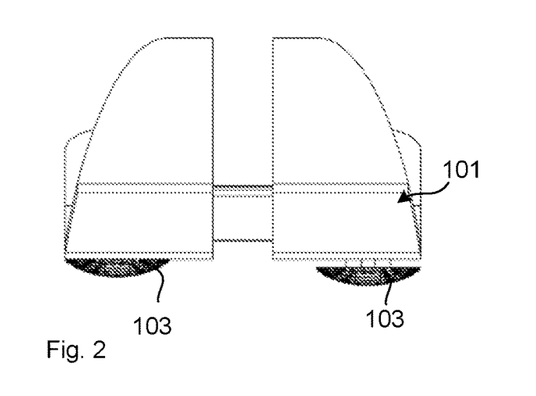
FIG. 2 is an anterior view of the surgical instrument.
Figure 3:
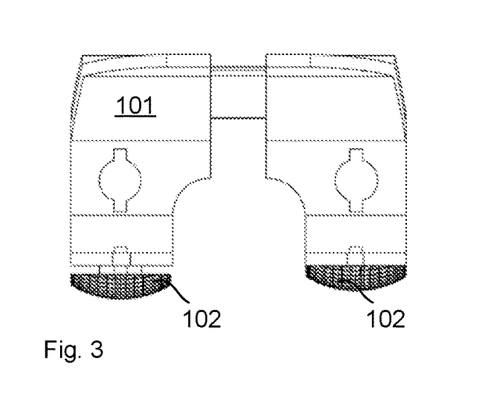
FIG. 3 is a top view of the surgical instrument.
Figure 4:
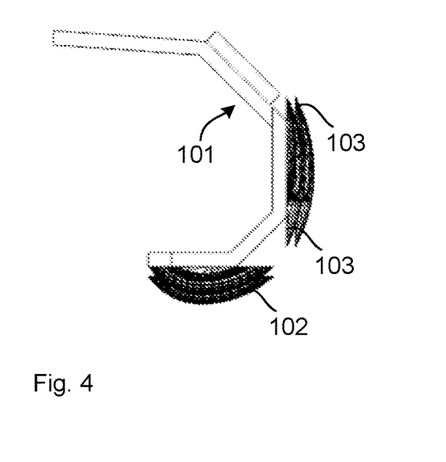
FIG. 4 is a side elevation of the surgical instrument.
Figure 5:
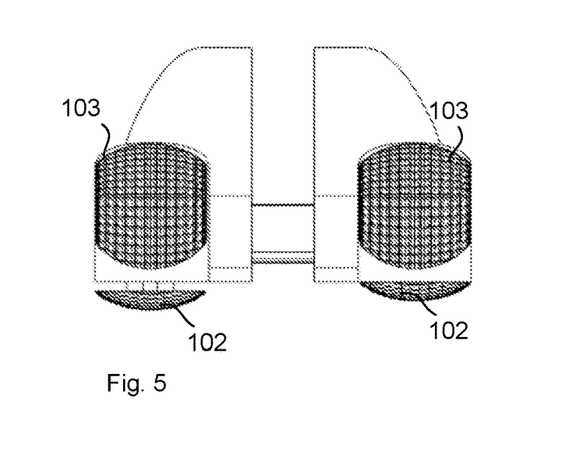
FIG. 5 is a posterior view of the surgical instrument.
Figure 6:
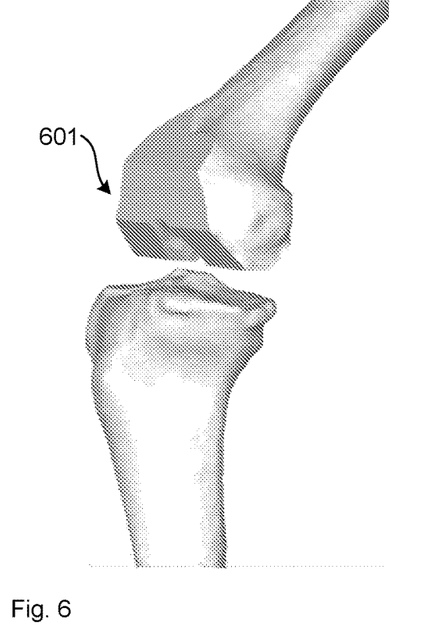
FIG. 6 illustrates a prepared distal end of a femur.
Figure 7:
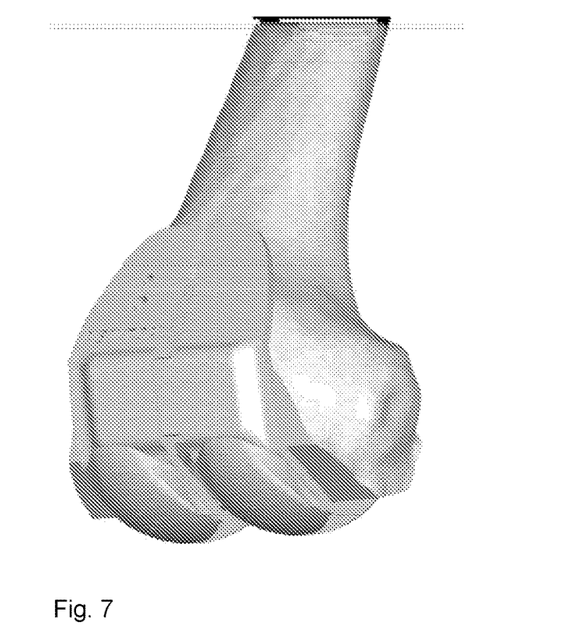
FIG. 7 illustrates the prepared distal end of the femur with the surgical instrument attached thereto.

FIG. 1 is a perspective view of a surgical instrument 100. FIGS. 2, 3, 4 and 5 also show the surgical instrument in different views and like numerals refer to like features of the instrument. Surgical instrument 100 comprises a contact surface 101 shaped to fit a prepared distal end of the femur as shown in FIG. 6 where the distal end is shown at 601. In one example, the preparation of the distal end 601 is according to a specification of a selected implant. This means, the femur is prepared to provide cut surfaces that interface with a given implant in the sense that the cut surfaces have cut angles that are identical to surface angles of the implant. It is noted that the implant is fitted to the femur at a later stage after the tibia has been prepared as well and after the surgical instrument 100 has been removed. But first, the surgical instrument is attached to the prepared distal end 601 of the femur as shown in FIG. 7.

Surgical instrument 100 comprises artificial posterior condyles 102 that imitate the posterior surface of the native condyles of the femur that have been removed by the preparation of the femur. Imitating in this context means that the artificial posterior condyles 102 have a similar shape to the native surface to the extent that the artificial posterior condyles can provide a similar function to the native surface. In particular, the artificial posterior condyles provide a similar function when bearing against the native tibia surface. Importantly, the artificial posterior condyles 102 are pivotable.

Figure 8A:
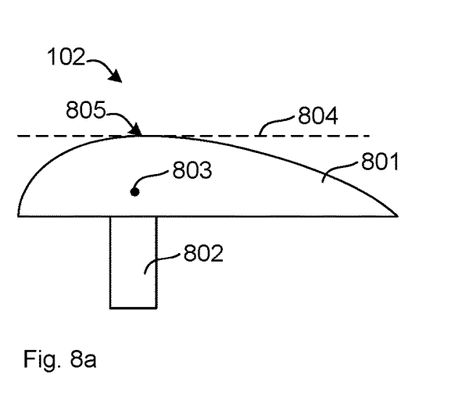
FIG. 8a is a side elevation of an artificial posterior condyle in upright (not pivoted) position.
Figure 8B:
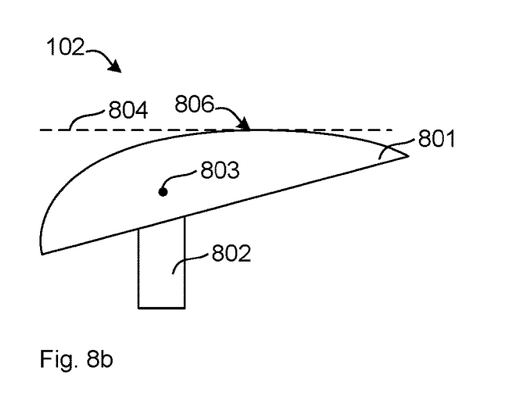
FIG. 8b is a side elevation of the artificial posterior condyle in a pivoted position.

FIG. 8a illustrates the artificial posterior condyle 102 in upright (not pivoted) position while FIG. 8b illustrates the artificial posterior condyle 102 in a pivoted position. Artificial condyle 102 comprises a head 801 and a post 802. The head 801 is pivotable about a (frontal) pivot axis 803 (shown as a dot due to the projection of the drawing). An imaginary contact surface 804 is also shown for illustrative purposes only. In this example, the pivot axis 803 lies within the head 801, which has an advantage over being located outside, such as at the bottom of post 802 as the rotating movement of head 801 provides a better balancing of the knee. In particular, it can be seen that a rotation of head 801 leads to a contact point 805 between the contact surface 804 and the head 801 in FIG. 8a moving backwards to contact point 806 in FIG. 8b. This imitates the behaviour of the knee joint during roll-back at 90 degrees flexion. It is also noted that the contact point 806 is higher (further away from device 100 than contact point 805. In effect, this simulates the addition of material within the knee joint.

It is noted that in FIGS. 8a and 8b the post 802 is rigid and the rotation is achieved by a bearing (not shown) within the head 801. However, in other examples, post 802 is flexible to allow the pivoting of the head 801. For example, the post 802 may be rectangular and relatively flat to allow flexion/pivoting in forward/backward direction but restrict pivoting in sidewards direction. The flat post may be segmented into multiple posts.

Further, post 802 may be designed so that it allows distraction (i.e. lateral displacement) of the head 801 relative to the surgical instrument 100. In other words, post 802 may allow the head 801 to move closer or further away from the base of the post 802. This is visible in FIGS. 3 and 5 where the left condyle is distracted further than the right condyle. It is noted that the distraction can be set by the surgeon, such as by turning a screw, and then it is locked so that the distraction does not change when the surgeon moves the knee.

Interestingly, the surgeon can now flex the knee and move the femur relative to the tibia until a desired tightness/looseness is achieved. At that moment, the flexion angle of the knee defines a slope of a tibial cut by way of a cutting block that is fixed on the tibia and adjustable in slope.

Figure 9:
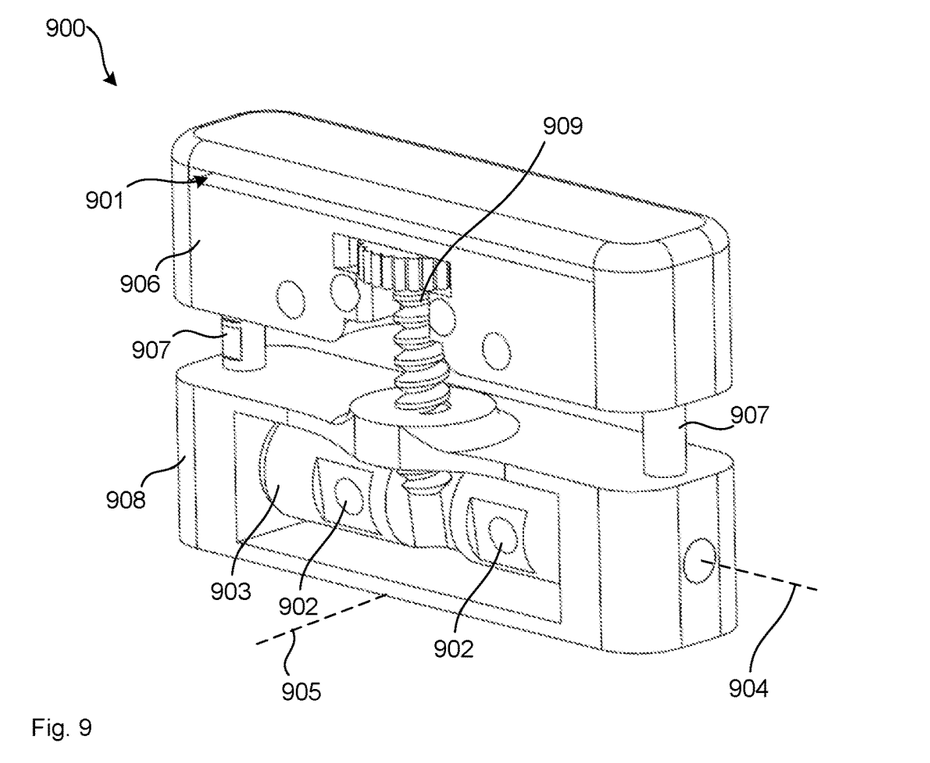
FIG. 9 is a perspective view of a cutting block.

FIG. 9 illustrates a cutting block 900 comprising a slot 901 for insertion of a blade and two pin holes 902 to receive respective guide pins. The pin holes 902 extend through a cylinder 902 that pivots about cylinder axis within cutting block 900. As a result, when the pins are fixed on the tibia, the cutting block is fixed in rotation about the sagittal axis 905 but pivotable about frontal axis 904. Further, the slot 901 is defined by a head 906 that is slidably engaged with pins 907 to a base 908 housing the cylinder 903. The distance between the head 906 and the base 908 is set by a screw drive 909 to thereby adjust the cutting depth.

Rotation of the cylinder 903 defines the rotation about the frontal axis 904, which also defines the slope of the cut through slot 901. This means, the cutting block can be adjusted in slope through rotation of cylinder 903 so that the cut (slot 901) is in parallel to the standard plane of the femoral component as will be described in more detail below.

As shown in FIGS. 1, 2, 4 and 5, the surgical instrument also comprises artificial distal condyles 103 that imitate the distal surface of the native condyles and may also be distractable as described above in relation to the artificial posterior condyles.

In particular, distraction of one of the artificial posterior condyle and the artificial distal condyle causes distraction of the other of the artificial posterior condyle and the artificial distal condyle. In other words, the posterior and distal condyles on each side are coupled such that they are distracted by about the same distance. That is, the artificial medial distal condyle is coupled to the artificial medial posterior condyle and vice versa for the lateral side. For example, there may be a mechanical coupling comprising screws and the like, pneumatic coupling or electric coupling through the user of electric or magnetic actuators controlled by wires.

Figure 10:
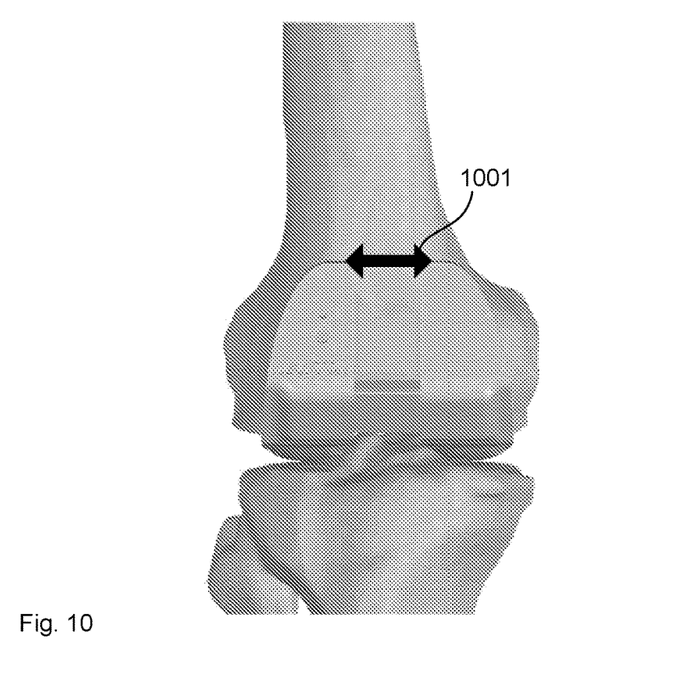
FIG. 10 illustrates another example of the surgical instrument that is laterally adjustable.

FIG. 10 illustrates another example where the surgical instrument comprises a lateral and a medial half which are slidably engaged with each other. The surgeon can expand the device mediolaterally until the distal femoral condyles are sitting at the most distal portions of the native articulate tibial compartments as indicated by arrow 1001.

Figure 11:
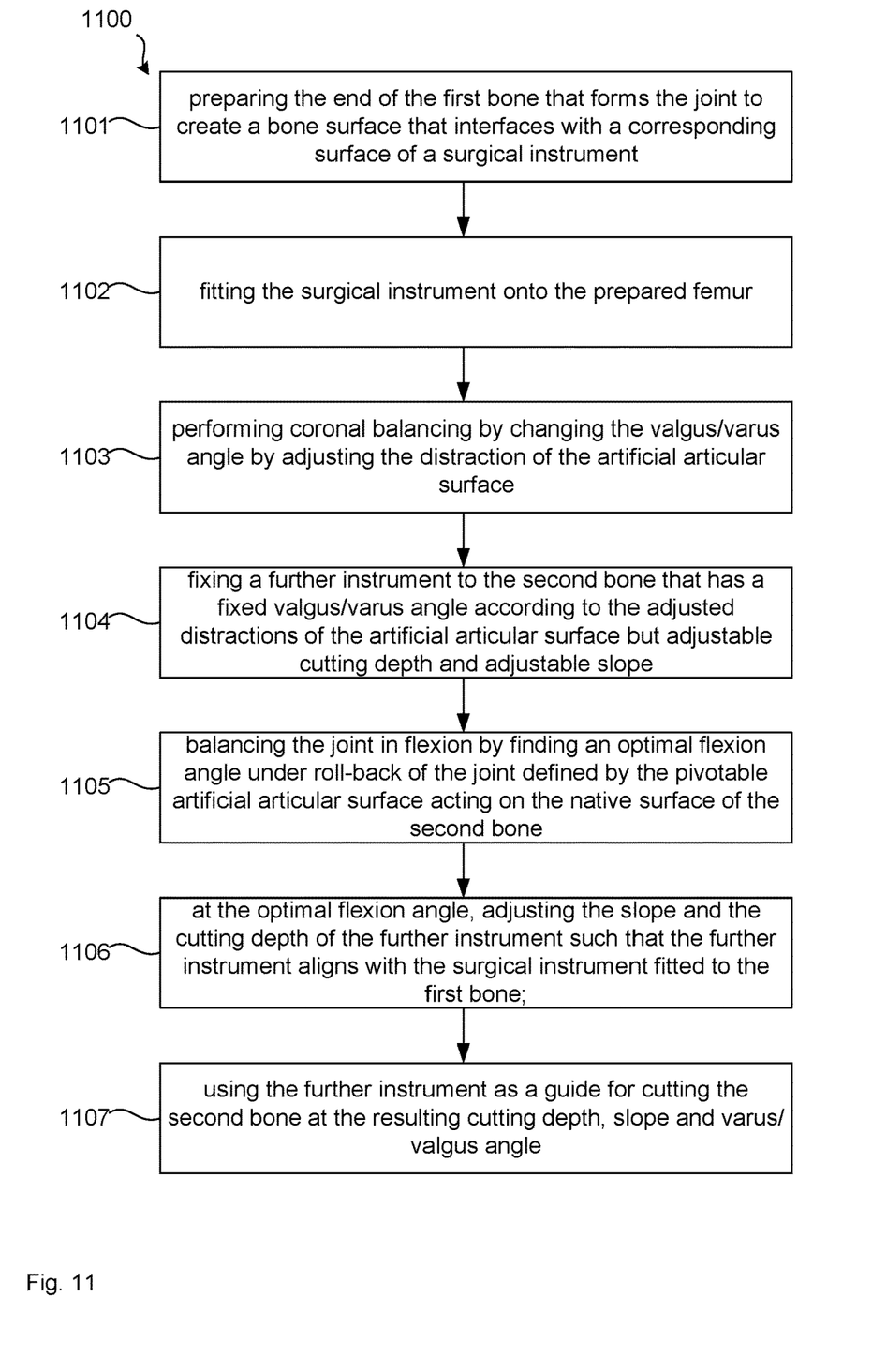
FIG. 11 illustrates a method for total knee replacement.
Figure 12:
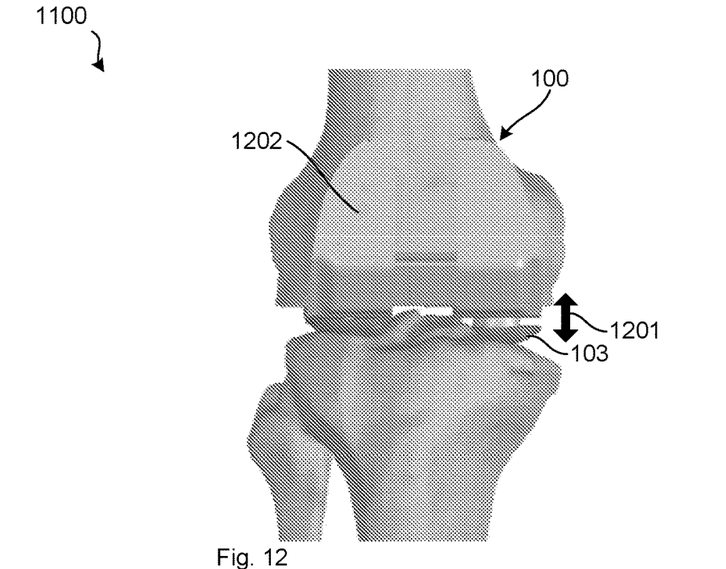
FIG. 12 illustrates coronal balancing by adjusting the distraction of one of the distal condyles.
Figure 13A:
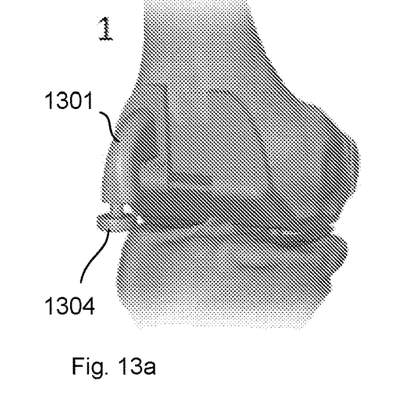
FIGS. 13a to 13d illustrate the steps of attaching an outrigger and a marking block to the surgical instrument.
Figure 13B:
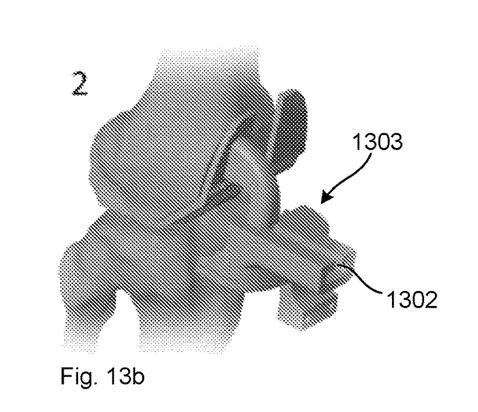
Figure 13C:
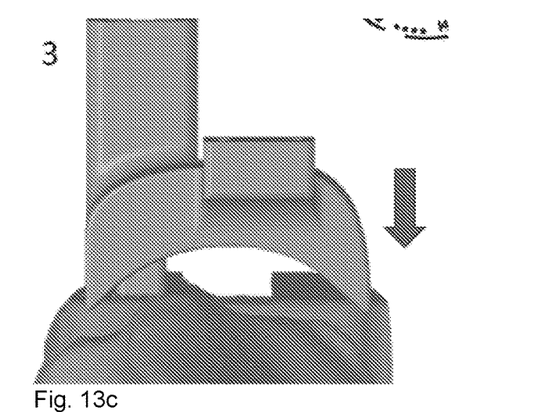
Figure 13D:
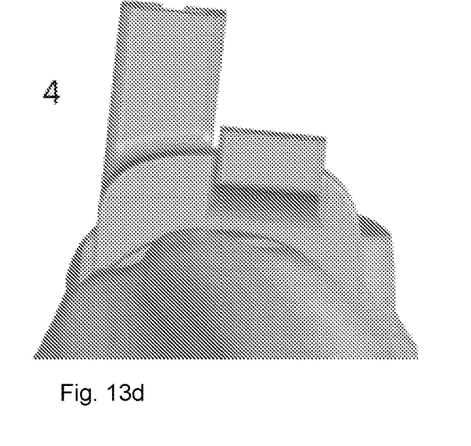

FIG. 11 illustrates a method 1100 for total replacement of a joint between a first bone (e.g. femur) and a second bone (e.g. tibia). The method 1100 comprises preparing 1101 the end of the bone that forms the joint (e.g. distal end of the femur) to create a bone surface that interfaces with a corresponding surface of a surgical instrument as shown in FIG. 6. The surgical instrument comprises artificial articular surfaces (e.g. distal condyles 103) that are distractable and further artificial articular surfaces (e.g. posterior condyles 102) that are distractable and pivotable as described above. The next step is fitting 1102 the surgical instrument 100 onto the prepared femur. Now, the surgeon performs 1103 coronal balancing by changing the *valgus/varus* angle by adjusting the distraction of the artificial articular surfaces (distal and/or posterior condyles). FIG. 12 illustrates the coronal balancing by adjusting the distraction of one of the distal condyles 103 as indicated by the arrow 1201. It is noted that in this example, surgical instrument 100 further comprises holes 1202 to mount an outrigger as described below.

The next step is fixing 1104 a further instrument (such as a tibial instrument) to the second bone (e.g. tibia) that has a fixed *valgus/varus* angle according to the adjusted distractions of the artificial condyles but adjustable cutting depth and adjustable slope. FIGS. 13a to 13d illustrate this step in more detail. The surgeon attaches an outrigger 1301 as pictured onto the locating holes 1202 on the instrument 100 and places a rail 1302 of an alignment block 1303 onto a corresponding disk 1304 of the outrigger 1301.

Figure 14:
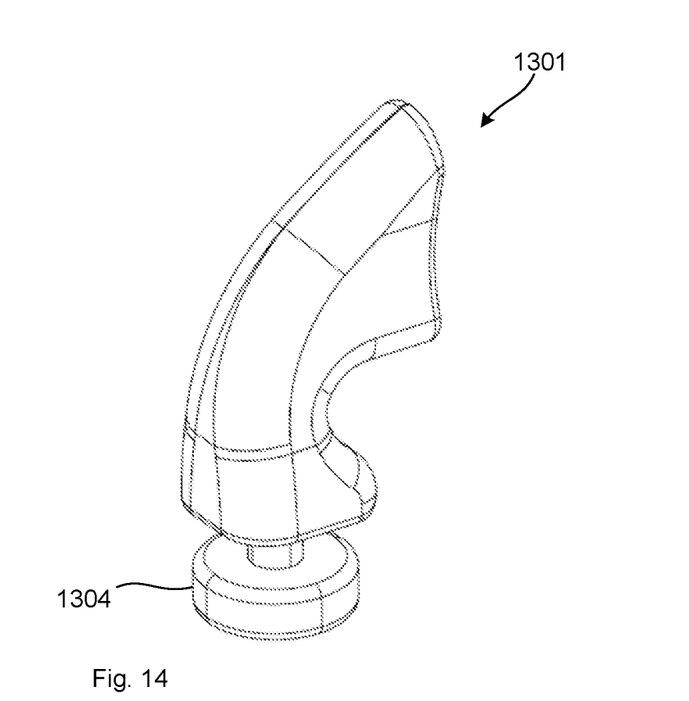
FIG. 14 is a perspective view of the outrigger used in FIGS. 13a to 13d.
Figure 15:
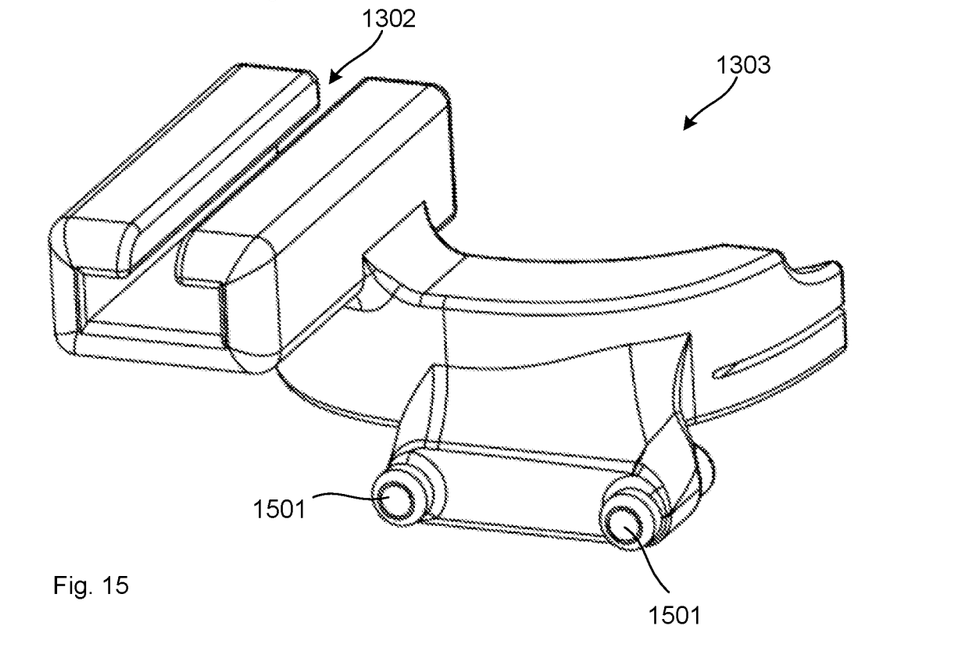
FIG. 15 is a perspective view of the marking block used in FIGS. 13a to 13d.
Figure 16A:
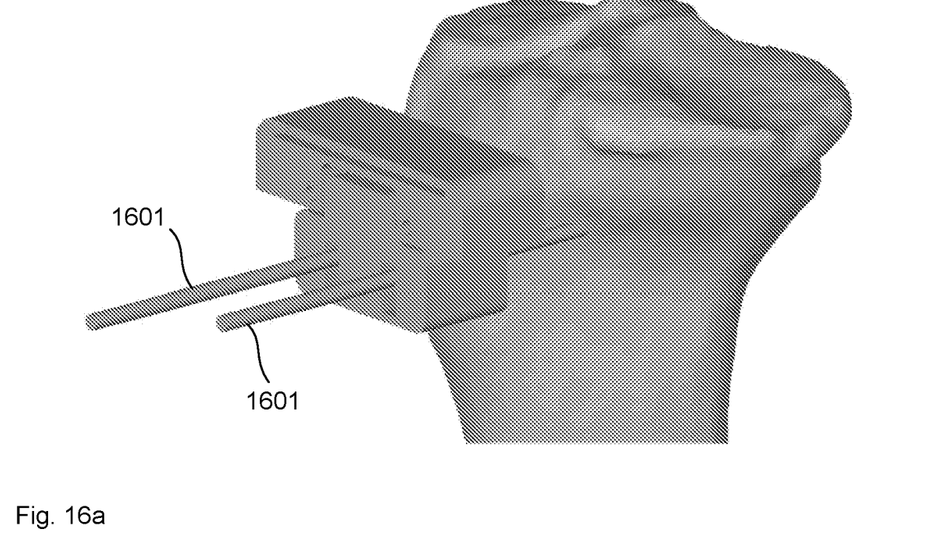
FIGS. 16a and 16b illustrate the attachment of the cutting block with pins to the tibia.
Figure 16B:
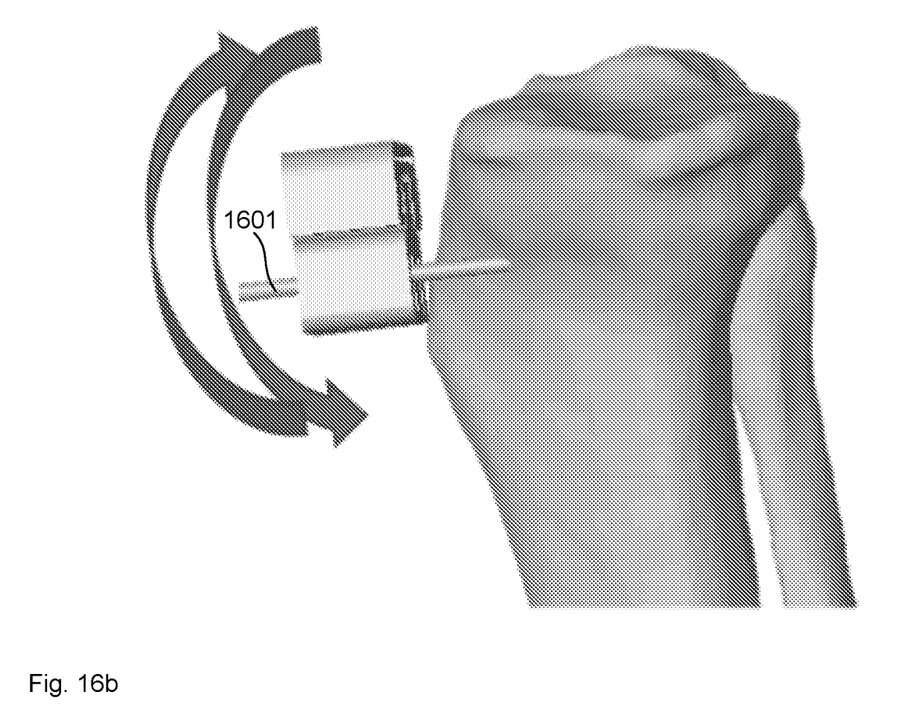

FIG. 14 illustrates the outrigger 1301 comprising the disk 1304 and FIG. 15 illustrates an alignment block 1303 comprising a rail 1302 to receive disk 1304 of outrigger 1301. The alignment block 1303 can be used when the marking block is in place, to make diathermy marks on the tibia. The surgeon can then bring the knee into flexion and attach the outrigger 1301 to the artificial distal condyle 103, balance the knee and apply a second set of diathermy marks on the tibia. The knee is then brought back into extension and the outrigger 1301 mounted onto the holes 1202. A final tibial coronal alignment decision can be made based on both flexion and extension diathermy markings. Importantly, marking block 1303 comprises two marking holes 1501 which allows the tibial coronal alignment to be locked by setting two distal setting pins through the marking holes 1501. Finally, the surgeon places the tibial cutting block 900 as shown in FIG. 9 on the pre-located pins such that the pin holes 902 of the cutting block slide over the pins such that the head 906 extends proximally from the base 908. As described above, this fixes the rotation about sagittal axis 905 while keeping slope and cutting depth variable which is also illustrated in FIGS. 16a and 16b where pins 1601 are shown.

Once the coronal balancing is complete and the cutting block 900 is in place, the surgeon balances 1105 the joint in flexion by finding an optimal flexion angle under roll-back of the joint defined by the pivotable artificial posterior condyles acting on the native tibia. In other words, the surgeon uses a slope outrigger and sets the cutting block 900 parallel to the 0 degrees posterior condyle tilt setting. Then, the surgeon places the joint in flexion, assesses the anterior/posterior (AP) stiffness of the joint and adjusts the posterior condylar tilt (rotation, pivot as shown in FIGS. 8a and 8b) accordingly.

Figure 17A:
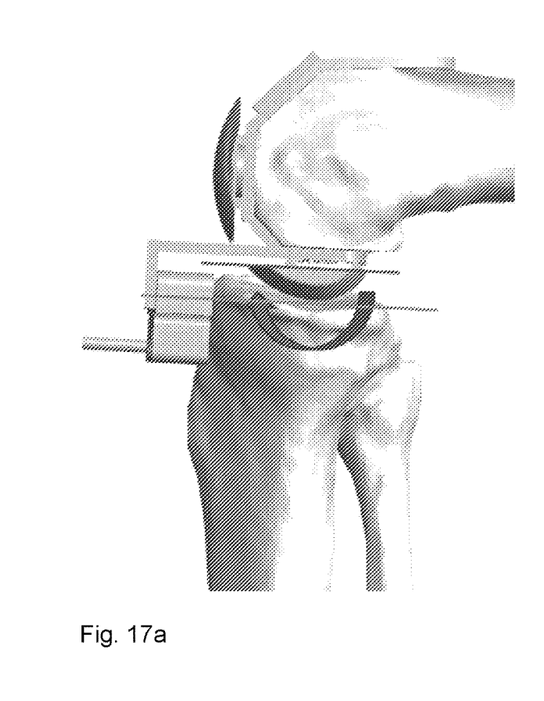
FIG. 17a shows a rotation of the artificial posterior condyle.
Figure 17B:
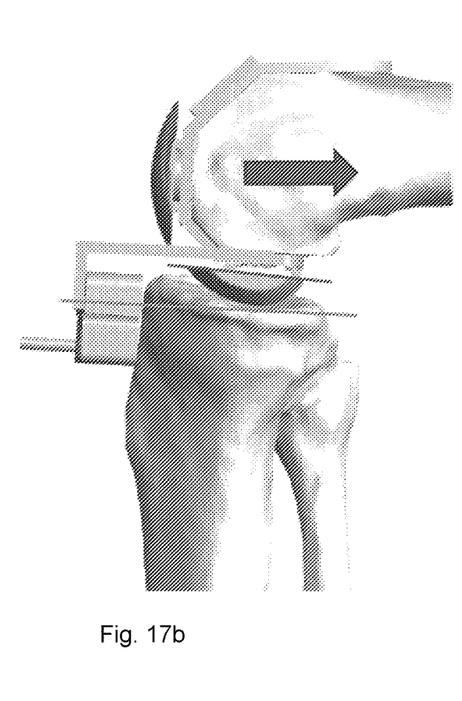
FIGS. 17b and 17c show roll-back movement of the knee joint and the corresponding change in condyle rotation.
Figure 17C:
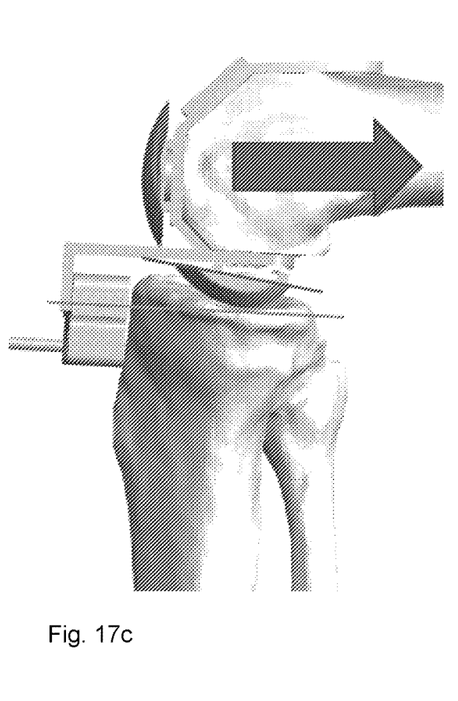

FIG. 17a shows a rotation of the artificial posterior condyle 102, while FIGS. 17b and 17c show roll-back movement of the knee joint and the corresponding change in condyle rotation. Finally, the surgeon flexes the knee joint to be parallel to the posterior condylar tilt desired following AP stiffness balancing.

Figure 18:
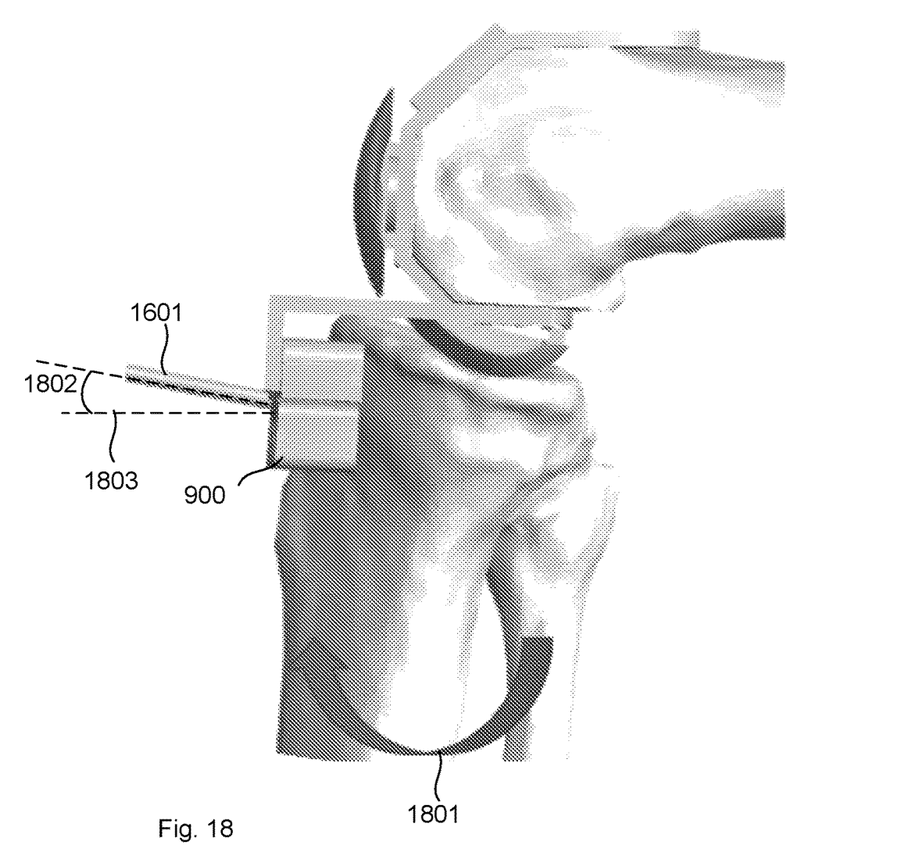
FIG. 18 shows how rotation of the tibia now changes the slope of the cut defined by the cut block.

FIG. 18 shows how rotation 1801 of the tibia now changes the slope of the cut defined by the cut block 900. In particular, there is now a prominent angle 1802 visible between the pins 1601 and the cut direction 1803. That is, at the optimal flexion angle, the surgeon can adjust 1106 the slope and the cutting depth of the tibial instrument such that the tibial instrument aligns with the surgical instrument fitted to the femur.

Figure 19:
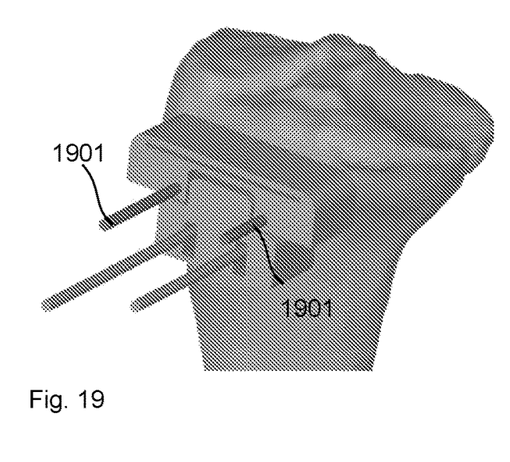
FIG. 19 illustrates the locking of the overall tibial alignment.
Figure 20:
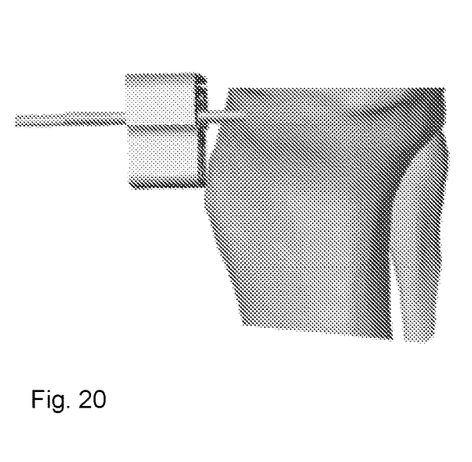
FIG. 20 shows the result of performing a tibial cut.

FIG. 19 shows how the overall tibial alignment can be locked by transferring the desired tibial slope to the proximal non-pivoting pins 1901. FIG. 20 shows how the cutting block can be used (step 1107 in FIG. 11) as a guide for cutting the tibia at the resulting cutting depth, slope and *varus/valgus* angle.

The surgical instrument described above provides an advantage to the surgeon as it allows the balancing of the knee and the successive locking of degrees of freedom to thereby reduce the degrees of freedom in the remaining steps. While this leverages the experience of the surgeon in feeling the patient's knee, there is also an opportunity to further assist the surgeon in ways that are not offered by existing devices. That is, surgical device 100 may comprise sensors that provide feedback to the surgeon about the current mechanical properties of the knee and in particular the current tightness/looseness of the knee. In particular, the artificial posterior condyles 102 may comprise pressure sensors to assist in balancing the knee. For example, post 802 shown in FIGS. 8a and 8b may incorporate a piezoelectric sensor or other pressure sensor. Similarly, the anterior condyles 103 may also comprise pressure sensors. This means that when the surgeon balances the knees and adjust the distraction of the condyles there can be a display in the theatre that shows the pressure for all or some of the condyles. In other examples, there may simply be a light that changes from red to green when at least a threshold pressure is detected to show that each condyle is engaged. That is, there may be an external device with four lights (one for each condyle) and as the surgeon moves the knee and adjusts the distractions, the lights change between red and green to show the surgeon when the condyles a properly engaged with the native tibia surface.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A surgical instrument for surgery on a joint between a first bone and a second bone, the surgical instrument comprising;
   a contact surface shaped to fit a prepared end of the first bone of the joint; and
   an artificial articular surface opposite the contact surface, wherein the artificial articular surface is configured to imitate a native articular surface of the first bone that has been removed by the preparation of the first bone, wherein the artificial articular surface comprises;
   a first artificial posterior condyle, wherein the first artificial posterior condyle includes a first posterior condyle head and a first posterior condyle post, wherein the first posterior condyle head is pivotably couple to the first posterior condyle post, and wherein the first artificial posterior condyle is configured to be coupled to the contact surface via the first posterior condyle post; and
   a first artificial distal condyle, wherein the first artificial distal condyle includes a first distal condyle head and a first distal condyle post, wherein the first distal condyle head is pivotably coupled to the first distal condyle post, and wherein the first artificial distal condyle is configured to be coupled to coupled to the contact surface via the first distal condyle post.

2. The surgical instrument of claim 1, wherein the artificial articular surface is convex and configured to interface with a concave native articular surface of the second bone of the joint.

3. The surgical instrument of claim 1, wherein each of the first artificial posterior condyle and the first artificial distal condyle are adjustable and lockable in a distraction position relative to the contact surface to define a distance of the artificial articular surface to the contact surface.

4. The surgical instrument of claim 1, further comprising: a cutting block, wherein a slope of a cut to the second bone is defined by the cutting block, wherein the cutting block is configured to be adjustable to adjust the slope, and wherein a flexion angle of the joint defines a slope of the cut to the second bone.

5. The surgical instrument of claim 4, wherein the cutting block is configured to be adjusted in slope so that the cut is in parallel to a standard plane of the surgical instrument.

6. The surgical instrument of claim 4, wherein the cutting block is adjustable to adjust a cutting depth.

7. The surgical instrument of claim 1, wherein the contact surface corresponds in shape to a contact surface of a component of an implant.

8. The surgical instrument of claim 1, wherein the artificial articular surface is similar in shape and location to the native surface of the first bone.

9. The surgical instrument of claim 1, wherein each of the first artificial posterior condyle and the first artificial distal condyle are pivotable relative to the first posterior condyle post and the first distal condyle post, respectively, such that pivoting of each of the first artificial posterior condyle and the first artificial distal condyle are increases a distance of each of the first artificial posterior condyle and the first artificial distal condyle are from the contact surface.

10. The surgical instrument of claim 9, wherein each of the first artificial posterior condyle and the first artificial distal condyle are pivotable about a frontal pivot axis of the first posterior condyle post and the first distal condyle post, respectively, that is located within the artificial articular surface.

11. The surgical instrument of claim 1, further comprising a cutting block that is attachable to the second bone of the joint in a first configuration where a first portion of the cutting block is fixed in relation to a sagittal axis and a second portion of the cutting block is pivotable about a frontal axis to adjust a slope of a cut on the second bone based on the pivoting of the artificial articular surface.

12. The surgical instrument of claim 1, wherein the artificial articular surface comprises pressure sensors to assist in balancing the joint.

13. The surgical instrument of claim 1, wherein each of the first artificial posterior condyle and the first artificial distal condyle are movable relative to the contact surface to allow translation to define an interior-exterior rotation of the second bone.

14. The surgical instrument of claim 1, wherein the joint is a knee joint and the first bone is the femur of the knee.

15. The surgical instrument of claim 14, wherein the first artificial posterior condyle is configured to imitate a posterior surface of a native condyle of the femur and wherein the first artificial distal condyle is configured to imitate a distal surface of the native condyle of the femur.

16. The surgical instrument of claim 15, wherein for one of medial and lateral sides the artificial posterior condyle and the artificial distal condyles are distractable relative to the contact surface and distraction of one of the artificial posterior condyle and the artificial distal condyle causes distraction of the other of the artificial posterior condyle and the artificial distal condyle.

* * * * *

UNITED STATES PATENT AND TRADEMARK OFFICE
CERTIFICATE OF CORRECTION

PATENT NO. : 11,931,050 B2
APPLICATION NO. : 17/253853
DATED : March 19, 2024
INVENTOR(S) : Brad Miles et al.

Page 1 of 1

It is certified that error appears in the above-identified patent and that said Letters Patent is hereby corrected as shown below:

In the Claims

At Column 8, Line 59 (Claim 1), please delete "to coupled".

Signed and Sealed this
Twenty-seventh Day of August, 2024

Katherine Kelly Vidal
*Director of the United States Patent and Trademark Office*